United States Patent [19]

John

[11] Patent Number: 5,072,739

[45] Date of Patent: Dec. 17, 1991

[54] ISCHEMIA-REPERFUSION TUMOR THERAPY

[76] Inventor: Angelo P. John, 106 Henry St., St. Green, Conn. 06830

[21] Appl. No.: 710,778

[22] Filed: Jun. 5, 1991

[51] Int. Cl.⁵ .............................................. A61B 19/00
[52] U.S. Cl. .................................... 128/897; 128/898
[58] Field of Search ............... 128/897, 898, DIG. 12, 128/DIG. 13; 604/96-99, 101, 103

[56] References Cited

U.S. PATENT DOCUMENTS 5,036,868 8/1991 Borggren et al. ..................... 604/96

Primary Examiner—Ronald Frinks
Assistant Examiner—K. M. Reichle
Attorney, Agent, or Firm—Charles J. Herron

[57] ABSTRACT

A method of treating solid tumors by (a) occluding the supply of oxygenated blood to the tumor to be treated for a period sufficient to induce hypoxia; (b) reperfusing the tumor with the blood occluded in (a) for a period sufficient for oxygen-derived free radicals to form and effect reperfusion injury to the tumor; and (c) repeating steps (a) and (b) until the desired degree of tumor remission is achieved.

10 Claims, No Drawings

ISCHEMIA-REPERFUSION TUMOR THERAPY

BACKGROUND OF THE INVENTION

1. Field of the Invention

This invention relates to vascular catheterization therapy techniques, and particularly to an improvement in transcatheter arterial embolization (TAE) treatment of solid tumors.

2. Brief Description of the Prior Art

Vascular catheterization techniques have improved greatly in recent years and have evolved from their original use in diagnosis to include therapeutic applications as well. One area of such therapeutic uses is therapeutic embolization, with several reports of successful use of embolization for treating malignant tumors.

Transcatheter arterial embolization (TAE) of abdominal tumors, particularly hepatic and renal tumors, has become an integral part of their therapy. For background regarding the use of TAE in treatment of hepatic tumors, see Chuang et al, *Semin. Roentgenol.*, 16: 13–25(1981); Chuang et al, *Radiology*, 133: 611–614(1979); Chuang and Wallace, *Cardiovasc. Intervent. Radiol.*, 3: 256–267(1980); and Wallace et al, *Radiology*, 138: 563–570(1981). See also, Wheeler et al, *Br. Med. J. [Clin Res]*, 2: 242–244(1979) and Clouse et al, *Radiology*, 147: 407–411(1983). Regarding TAE treatment of renal cell carcinoma, see Goldstein et al, *Am. J. Radiol.*, 123: 557–562(1975) and Hlava et al, *Radiology*, 121: 323–329(1976).

TAE is regarded as particularly effective for hepatocellular carcinomas. Yamada et al, *Radiology*, 148: 397–401(1983) reports the use of TAE in over a hundred cases of unresectable hepatomas. A vascular catheter was inserted into the hepatic artery that fed the tumor and used to feed a gelatin sponge block impregnated with antineoplastic agent and a contrast medium. Care was required to prevent the backflow of pieces of the sponge block into proximal arteries. See also, Katsushima et al, *Radiology*, 174: 747–750(1990).

GELFOAM® particles are readily available in whatever size is needed and are usually used as the embolic material. However, GELFOAM® particles occlude the major feeding vessels but not the minute tumor vessels. The response to this has been attempts to use other embolic materials such as small IVALON® particles and ferropolysaccharides. See Chuang et al, *Am. J. Radiol.*, 136: 729–733(1981) and Sako et al, *Invest. Radiol.*, 17: 573–582(1982), respectively.

Ohishi et al, *Radiology*, 154: 25–29(1985) reports the use of TAE in treatment of hepatocellular carcinoma cases where surgical intervention was considered impossible. GELFOAM® particles were introduced as the embolic material into the catheter following angiographically controlled infusion of an ETHIODOL®-anticancer agent emulsion via the appropriate hepatic artery. This combined therapy is said to have the dual effects of occlusion of peripheral vessels, including tumor vessels, by the ETHIODOL®-anticancer agent emulsion, followed by embolization of the main feeding vessels with Gelfoam particles.

Thus, TAE has been developed as a therapeutic technique for permanent occlusion of the blood supply to solid tumors, such as in the reports identified above, and often also as a means for delivering antineoplastic agents to the tumor site as emulsions or impregnated in the occluding material.

Separate from the progress in the above field, compounds such as streptokinase and tissue-type plasminogen activator (TPA) have been used in the treatment of coronary artery occlusions. One of the major problems encountered has been the tissue damage occurring after reperfusion has been established. Recent evidence suggests that oxygen-derived free radicals may be abundantly produced in ischemic tissues, accounting for at least part of the damage that results. Oxygen-derived free radicals include the superoxide anion, produced by the one-electron reduction of dioxygen, the hydroxyl radical and singlet oxygen.

Ischemia, by itself, will ultimately produce tissue death if it is sufficiently severe and prolonged. However, much of the injury may occur during reperfusion, rather than during the period of hypoxia. Occluded blood does not contain free radicals. Occluded blood contains oxygen which is converted by hypoxanthine and xanthine oxidase to oxygen-derived free radicals after reperfusion. The mechanism and effects of the sequence of reactions that produce the superoxide and other oxygen-derived cytotoxic species is reviewed in McCord, N. *Eng. J. Med.*, 312: 159–163(1985).

Thus, their removal has become the focus of study leading to the use of compounds such as superoxide dismutase or the avoidance of streptokinase or TPA as emergency therapeutic agents altogether.

When generated in the media surrounding cells in tissue culture, oxygen species, particularly hydrogen peroxide, have been reported to lyse tumor cells. See, Simon et al, *J. Biol. Chem.*, 256: 7181–7186(1981); Granger et al, *J. Clin. Invest.*, 65: 357–370(1980); Nathan et al, *J. Exp. Med.*, 149: 84–99(1979); Clark and Klebanoff, *J. Exp. Med.*, 141: 1442–1447(1975); and Clark et al, *Blood*, 45: 161–170(1975). However, it is noteworthy that Simon et al conclude that hydrogen peroxide is the agent responsible for cell death and that no direct effect was attributable to superoxide anions, hydroxyl radicals or singlet oxygen.

TAE has met with some success in the treatment of solid tumors and some researchers have investigated the effect of oxygen species on tumor cells. However, the above work has not brought these areas of clinical treatment and experimental investigation together, particularly in any way for their combined use in a clinical regimen for treating solid tumors.

THE INVENTION

This invention revises the approach to TAE by combining the tumor damaging effects of embolization-induced ischemia with the destructive effects of reperfusion of the tumor with endogenously formed, accumulated oxygen-derived free radicals.

Thus, a principal aspect of the invention is a method of treating solid tumors by (a) occluding the supply of oxygenated blood to the tumor to be treated for a period sufficient to induce hypoxia in the tumor; (b) reperfusing the tumor with the blood occluded in (a) for a period sufficient for oxygen-derived free radicals to form and effect reperfusion injury to the tumor; and (c) repeating steps (a) and (b) until the desired degree of tumor remission is achieved. The therapeutic regimen is an alternating cycle of occlusion and reperfusion of the major arterial blood supply of the tumor to be treated.

A balloon catheter is introduced into the patient and passed to the artery supplying the tumor to be treated. The catheter remains resident in the artery throughout the course of therapy. Ischemia and reperfusion are controlled by inflation, such as with a water soluble contrast medium, and deflation of the balloon so as to alternately block and pass blood flow to the tumor. Catheters that are now used in conventional ischemia therapy are suitable for use in the invention. They are available, for example, from Becton-Dickinson(Sandy, Utah), Meditech(Ontario, Canada) and Miller Instruments(Houston, Tex.). The particular choice of catheter will depend primarily on the inner diameter of the artery whose flow is to be occluded. Typically, these range from 1/30 inch to 1 inch catheter diameter.

Occlusion or embolization of the arterial blood supply in each occlusion and reperfusion cycle is for about one-half to 24 hours, preferably 1 to 6 hours, and particularly for a period of about 3 hours.

Reperfusion of the arterial blood supply in each occlusion and reperfusion cycle is permitted for that period during which the reperfusing blood contains a significant level of endogenously formed oxygen-derived free radicals and hydrogen peroxide to the tumor. This is generally over a range of about 10 minutes to 1-2 hours, preferably about 1 hour.

Currently, where the preferred durations of occlusion for about 3 hours and reperfusion for about 1 hour are used, the cycle is preferably repeated 3 to 6 times per day, each day until the desired degree of tumor remission is achieved. The desired degree of remission can be, for example, remission sufficient to render the tumor surgically removable or can be complete remission, i.e. no detectable remaining tumor cells.

The period of reperfusion is determined individually in each case based on the rate of free radical level decay in the reperfused blood. It is independent of the duration of occlusion, as these exert different, independent toxic effects on the tumor being treated.

What is claimed is:

1. A method of treating solid tumors which comprises:
   (a) occluding the supply of oxygenated blood to the tumor to be treated for a period sufficient to induce hypoxia in the tumor;
   (b) reperfusing the tumor with the blood occluded in (a) for a period sufficient for oxygen-derived free radicals to form and effect reperfusion injury to the tumor; and
   (c) repeating steps (a) and (b) until the desired degree of tumor remission is achieved.

2. The method of claim 1 wherein the occlusion of step (a) is for about one-half to 24 hours.

3. The method of claim 2 wherein the occlusion is for about 1 to 6 hours.

4. The method of claim 3 wherein the occlusion is for about 3 hours.

5. The method of claim 1 wherein the reperfusion of step (b) is for about 10 minutes to 2 hours.

6. The method of claim 5 wherein the reperfusion is for about 10 minutes to 1 hour.

7. The method of claim 6 wherein the reperfusion is for about 1 hour.

8. The method of claim 1 wherein the occlusion of step (a) is for about 3 hours and the reperfusion of step (b) is for about 1 hour.

9. The method of claim 8 wherein steps (a) and (b) are alternatingly repeated 3 to 6 times per day.

10. The method of claim 1 wherein the occlusion of step (a) is by inflating an intraarterial balloon catheter positioned in an artery providing the supply of oxygenated blood to the tumor to be treated and the reperfusion of step (b) is by deflation of the catheter's balloon.

* * * * *